(12) United States Patent
Himeno et al.

(10) Patent No.: US 10,793,448 B2
(45) Date of Patent: Oct. 6, 2020

(54) DEHYDRATION OF WATER CONTAINING SOURCE OF FORMALDEHYDE, AND A METHOD FOR PRODUCING AN ETHYLENICALLY UNSATURATED CARBOXYLIC ESTER

(71) Applicant: Lucite International UK Limited, Southampton (GB)

(72) Inventors: Yoshiyuki Himeno, Hiroshima (JP); Ken Ooyachi, Hiroshima (JP); Masahide Kondo, Hiroshima (JP)

(73) Assignee: Lucite International UK Limited, Southhampton (GB)

( * ) Notice: Subject to any disclaimer, the term of this patent is extended or adjusted under 35 U.S.C. 154(b) by 3 days.

(21) Appl. No.: 16/122,169

(22) Filed: Sep. 5, 2018

(65) Prior Publication Data

US 2019/0062181 A1 Feb. 28, 2019

Related U.S. Application Data

(60) Division of application No. 14/379,051, filed as application No. PCT/JP2013/054639 on Feb. 18, (Continued)

(51) Int. Cl.
*C02F 1/44* (2006.01)
*B01D 61/36* (2006.01)
(Continued)

(52) U.S. Cl.
CPC ............ *C02F 1/448* (2013.01); *B01D 61/362* (2013.01); *B01D 71/028* (2013.01); (Continued)

(58) Field of Classification Search
CPC ... B01D 61/362; B01D 11/0492; C02F 1/448; C07C 45/786; C07C 47/04
See application file for complete search history.

(56) References Cited

U.S. PATENT DOCUMENTS 4,035,291 A 7/1977 Chiang et al.
4,137,054 A * 1/1979 Miyake .................. C07C 45/79
95/121
(Continued)

FOREIGN PATENT DOCUMENTS

CN 1304396 A 7/2001
CN 101721920 A 6/2010
(Continued)

OTHER PUBLICATIONS

Office Action dated Aug. 18, 2015 for Chinese Application No. 201380016221.1.
(Continued)

*Primary Examiner* — Ryan B Huang
(74) *Attorney, Agent, or Firm* — Shumaker, Loop & Kendrick, LLP

(57) ABSTRACT

Disclosed are methods for dehydrating a water containing source of formaldehyde in which water is separated from the water containing source of formaldehyde using a zeolite membrane. In certain aspects, the water containing source of formaldehyde includes a separation enhancer having a relative static permittivity ranging from 2.5 to 20, and the water containing source of formaldehyde may further include methanol. In certain aspects, (meth)acrylic acid alkyl ester may be produced using the dehydrated source of formaldehyde.

2 Claims, 2 Drawing Sheets

Related U.S. Application Data 2013, now Pat. No. 10,093,559, which is a continuation of application No. PCT/JP2012/054498, filed on Feb. 17, 2012.

(51) Int. Cl.

| | | |
|---|---|---|
| *C07C 67/343* | (2006.01) | |
| *C07C 45/78* | (2006.01) | |
| *C07C 67/56* | (2006.01) | |
| *B01D 71/02* | (2006.01) | |
| *C02F 101/34* | (2006.01) | |

(52) U.S. Cl.
CPC .......... *C07C 45/786* (2013.01); *C07C 67/343* (2013.01); *C07C 67/56* (2013.01); *C02F 2101/34* (2013.01); *Y02P 20/582* (2015.11)

(56) References Cited

U.S. PATENT DOCUMENTS

| | | |
|---|---|---|
| 4,285,811 A | 8/1981 | Miyake et al. |
| 5,554,286 A | 9/1996 | Okamoto et al. |
| 6,478,929 B1 * | 11/2002 | Parten .................... C07C 45/83 203/17 |
| 2003/0134662 A1 | 7/2003 | Shah et al. |
| 2004/0000521 A1 | 1/2004 | Leland et al. |

FOREIGN PATENT DOCUMENTS

| | | |
|---|---|---|
| DE | 4337231 A1 | 5/1995 |
| DE | 10004562 A1 | 8/2001 |
| EP | 1930067 A1 | 6/2008 |
| GB | 1107234 A | 3/1968 |
| JP | H07-185275 A | 7/1995 |
| JP | 2006265123 A | 10/2006 |
| KR | 20110010645 A | 2/2011 |
| WO | 99/64387 A1 | 12/1999 |
| WO | 2008/146037 A1 | 12/2008 |
| WO | 2009141641 A1 | 11/2009 |

OTHER PUBLICATIONS

International Search Report for PCT/JP2013/054639 dated Apr. 26, 2013.

* cited by examiner

DEHYDRATION OF WATER CONTAINING SOURCE OF FORMALDEHYDE, AND A METHOD FOR PRODUCING AN ETHYLENICALLY UNSATURATED CARBOXYLIC ESTER

TECHNICAL FIELD

The present invention relates to a method for dehydration of water containing source of formaldehyde, and a method for producing (meth)acrylic acid alkyl ester.

BACKGROUND ART

Recently, a method for producing (meth)acrylic acid alkyl ester by reacting a carboxylic acid ester with formaldehyde in the presence of a catalyst (vapor-phase condensation reaction) has been developed. For example, when methyl propanoate is used as carboxylic acid ester, methyl methacrylate is obtained as shown in the following formula (I).

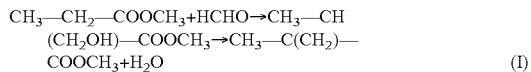

$$CH_3-CH_2-COOCH_3 + HCHO \rightarrow CH_3-CH(CH_2OH)-COOCH_3 \rightarrow CH_3-C(CH_2)-COOCH_3 + H_2O \quad (I)$$

Formaldehyde is used in the form of formalin in many cases. Formalin is an aqueous solution containing formaldehyde, and generally contains methanol as a stabilizer. Therefore, when formalin is used as a raw material of (meth)acrylic acid alkyl ester, water is introduced into the reaction system. When water is present in the reaction system, inhibition of the reaction progression and deterioration of the catalyst are more likely to occur.

A further reaction with an acetal is shown in the following formula (II).

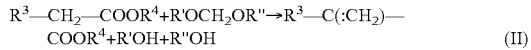

$$R^3-CH_2-COOR^4 + R'OCH_2OR'' \rightarrow R^3-C(:CH_2)-COOR^4 + R'OH + R''OH \quad (II)$$

A theoretical example of formula (II) with a dimethoxymethane is shown in the following formula (III).

$$CH_3-CH_2-COOR^4 + CH_3OCH_2OCH_3 \rightarrow CH_3-C(:CH_2)-COOR^4 + 2CH_3OH \quad (III)$$

The use of dimethoxymethane thus theoretically provides an anhydrous system which avoids the difficulty of subsequent water separation and/or subsequent product hydrolysis. In addition, the use of dimethoxymethane avoids the use of free formaldehyde but nevertheless acts in a general sense as a source of formaldehyde. The absence of water and free formaldehyde could greatly simplify the separation of methyl methacrylate from the product stream.

However, in practice, formula (III) is problematic because methanol dehydrates to dimethyl ether and water. In addition, dimethoxymethane decomposes under catalytic conditions to dimethylether and formaldehyde. Any water formed in these reactions can hydrolyse the ester feedstock or product to its corresponding acid which may be undesirable.

In addition, the presence of water in the reaction mixture increases catalyst decay so that the presence of water may be undesirable even in the production of ethylenically unsaturated carboxylic acids.

Therefore, when (meth)acrylic acid alkyl ester is produced, there is a demand to reduce the amount of water which is introduced to the reaction system, and, for example a method of dehydration by distillation of an aqueous solution of formaldehyde has been proposed (see PTL 1).

CITATION LIST

Patent Literature

[PTL 1] JP-A-2006-265123

SUMMARY OF INVENTION

Technical Problem

However, the method disclosed in PTL 1 had an insufficient dehydration performance.

The present invention is made from the viewpoint of these problems, and it provides a method for dehydration of a water containing source of formaldehyde having an excellent dehydration performance, and a method for producing (meth)acrylic acid alkyl ester using a dehydrated source of formaldehyde obtained by dehydration of the water containing source of formaldehyde.

Solution to Problem

According to a first aspect of the present invention, there is provided a method for dehydration of a water containing source of formaldehyde comprising the step of contacting the source of formaldehyde with a zeolite membrane in a manner effective to separate at least part of the water from the source of formaldehyde wherein the water containing source of formaldehyde comprises a separation enhancer having a relative static permittivity of between 2.5 and 20 at 20° C. and atmospheric pressure and wherein the water containing source of formaldehyde further contains methanol.

Preferably, the water is separated from the said water containing source of formaldehyde by zeolite membrane pervaporation or zeolite membrane vapor permeation, and more preferably, the water is separated by vapor permeation.

Typically, in the process of the invention, the water enriched fluid is the permeate and the dehydrated source of formaldehyde is the retentate. However, it is possible for the dehydrated source of formaldehyde to be the permeate and the water enriched fluid to be the retentate.

According to a further aspect of the present invention there is provided a method for producing an ethylenically unsaturated carboxylic ester, preferably, an α, β ethylenically unsaturated carboxylic ester by contacting a source of formaldehyde with a carboxylic acid ester in the presence of a catalyst, wherein a dehydrated source of formaldehyde is obtained by contacting a water containing source of formaldehyde with a zeolite membrane in a manner effective to separate at least part of the water from the water containing source of formaldehyde to produce the said dehydrated source of formaldehyde and the dehydrated source of formaldehyde is used as the said source of formaldehyde for the said method.

A particular preferred feature of the further aspect of the present invention is that the water containing source of formaldehyde contains a separation enhancer having a relative static permittivity of between 2.5 and 20, more preferably and according to the first or further aspects of the present invention the relative static permittivity is between 3 and 15, and most preferably between 4 and 10, especially, between 4 and 8 at 20° C. and atmospheric pressure.

By "atmospheric pressure" herein is meant 101.325 kPa.

By "relative static permittivity" is meant the ratio of the electric field strength in a vacuum to that in a given medium at a frequency of zero, this is commonly known as the dielectric constant.

It has been found that the separation enhancer carboxylic acid ester is particularly effective. The carboxylic acid ester is preferably methyl propanoate, methyl acrylate, methyl methacrylate, ethyl ethanoate or methyl ethanoate, more preferably, the carboxylic acid ester is methyl propanoate or methyl ethanoate, and most preferably, the carboxylic acid ester is methyl propanoate.

A preferred feature of the further aspect of the present invention is that a water containing source of the separation enhancer is combined with the water containing source of formaldehyde to produce a combined source and wherein the combined source is dehydrated in accordance with the first or further aspect of the invention to provide the said dehydrated source of formaldehyde which contains a separation enhancer. Whether the water containing source of formaldehyde is combined or otherwise, it may be contacted with the zeolite membrane in a batch process, a recycled batch process (i.e. repeated exposure of the same batch) or a continuous process. In a continuous process, a series of zeolite treatments with two or more membranes in series is also envisaged.

In preferred embodiments, the water containing source of formaldehyde and, optionally, the water containing source of the separation enhancer contains methanol.

It will be appreciated from the foregoing that the separation enhancer is not methanol. Typically, the separation enhancer is not a C1-C5 alkyl alcohol, more typically, it is not an alkyl alcohol, most typically, it is not an alcohol.

Typically, the ethylenically unsaturated ester is selected from the list consisting of methyl methacrylate and methyl acrylate.

The zeolite membrane is preferably a Linde Type-A zeolite membrane, more preferably, a Linde type-4A zeolite membrane.

The concentration of water in the water containing source of formaldehyde is preferably 0.5% by mass or more.

[1] A method for dehydrating a water containing source of formaldehyde comprising:
contacting the source of formaldehyde with a zeolite membrane in a manner effective to separate at least part of the water from the source of formaldehyde, wherein the water containing source of formaldehyde comprises a separation enhancer having a relative static permittivity of between 2.5 and 20 at 20° C. and atmospheric pressure and wherein the water containing source of formaldehyde further contains methanol.

[2] The method for dehydrating a water containing source of formaldehyde according to [1], wherein the manner is selected from the group consisting of zeolite membrane pervaporation or zeolite membrane vapor permeation.

[3] The method for dehydrating a water containing source of formaldehyde according to [2], wherein water is separated from the water containing source of formaldehyde by zeolite membrane vapor permeation.

[4] The method for dehydrating a water containing source of formaldehyde according to any one of [1] to [3], wherein the separated water is a permeate and, a dehydrated source of formaldehyde is a retentate.

[5] The method for dehydrating a water containing source of formaldehyde according to any one of [1] to [4], wherein the separation enhancer is carboxylic acid ester.

[6] The method for dehydrating the water containing source of formaldehyde according to claim 5, wherein the carboxylic acid ester is selected from methyl methacrylate, methyl acrylate, methyl propanoate ethyl ethanoate or methyl ethanoate.

[7] The method for dehydrating the water containing source of formaldehyde according to claim 6, wherein the carboxylic acid ester is methyl propanoate.

[8] The method for dehydrating the water containing source of formaldehyde according to any one of [1] to [7], wherein the zeolite membrane is a Linde Type-A or chabazite zeolite membrane.

[9] The method for dehydrating the water containing source of formaldehyde according to [8], wherein the zeolite membrane is a Linde Type-4A zeolite membrane.

[10] The method for dehydrating the water containing source of formaldehyde according to any one of [1] to [9], wherein the concentration of water in the water containing source of formaldehyde is at least 0.5% by mass based on 100% by mass of the water containing source of formaldehyde.

[11] A method for producing an ethylenically unsaturated carboxylic ester, preferably, an α, β ethylenically unsaturated carboxylic ester, comprising: contacting a dehydrated source of formaldehyde with a carboxylic acid ester in the presence of a catalyst,
wherein the dehydrated source of formaldehyde is obtained by contacting a water containing source of formaldehyde with a zeolite membrane in a manner effective to separate at least part of the water from the water containing source of formaldehyde to produce the said dehydrated source of formaldehyde.

[12] The method for producing an ethylenically unsaturated carboxylic ester according to [11], wherein the water containing source of formaldehyde further comprises a separation enhancer having a relative static permittivity of between 2.5 and 20 at 20° C. and atmospheric pressure.

[13] The method for producing an ethylenically unsaturated carboxylic acid ester according to [12] comprising: combining a water containing source of the separation enhancer with the water containing source of formaldehyde to produce a combined source, and dehydrating the combined source in accordance with the method for dehydrating the water containing source of formaldehyde according to [11] to provide a dehydrated source of formaldehyde which contains the separation enhancer.

[14] The method for producing an ethylenically unsaturated carboxylic acid ester according to any one of [12] to [13], wherein the separation enhancer is carboxylic acid ester.

[15] The method for producing an ethylenically unsaturated carboxylic acid ester according to any one of [11] to [14], wherein the water containing source of formaldehyde further contains methanol.

[16] The method for producing an ethylenically unsaturated carboxylic acid ester according to any one of [13] to [15], wherein the water containing source of the separation enhancer further contains methanol in addition to the separation enhancer.

[17] The method for producing an ethylenically unsaturated carboxylic acid ester according to any one of [11] to [16], wherein the ethylenically unsaturated acid ester is selected from the group consisting of methyl methacrylate and methyl acrylate.

Advantageous Effects of Invention

The present invention can provide a method for dehydration of the water containing source of formaldehyde having an excellent dehydration performance and a method for producing (meth)acrylic acid alkyl ester by using a dehydrated source of formaldehyde obtained by such dehydration.

DESCRIPTION OF EMBODIMENTS

Figure 1:
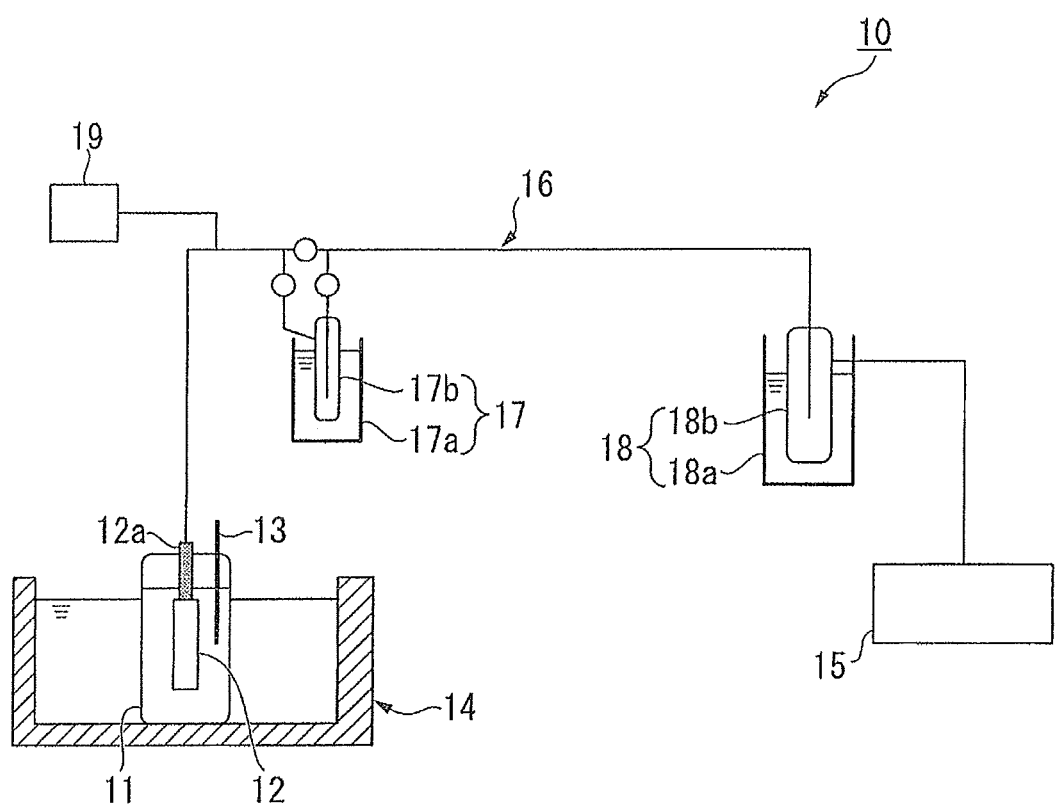
FIG. 1 is a schematic configuration view showing one example of a separation device where water is separated from the water containing source of formaldehyde.

The present invention will be described in detail below.

A method for dehydration of the water containing source of formaldehyde (hereinafter, simply referred to as "dehydration method") of the present invention separates water from water containing source of formaldehyde by using a zeolite membrane.

In the invention, a water containing source of formaldehyde is defined as a solution containing formaldehyde, water and an organic solvent other than formaldehyde. An example of a dehydrated source of formaldehyde is a solution where at least some water has been separated from the water containing source of formaldehyde. Generally herein, a "dehydrated source of formaldehyde" refers to a water containing source of formaldehyde that has had at least some water removed by the method of the present invention.

The water containing source of formaldehyde contains formaldehyde and water. Since formaldehyde is easily polymerized, the water containing source of formaldehyde preferably contains an organic solvent other than formaldehyde, for preventing polymerization of formaldehyde in the water containing source of formaldehyde. The organic solvent other than formaldehyde is not specifically limited, and various organic solvents can be used. Typically, however, by "organic solvents" mentioned herein is not meant the separation enhancer described below. A preferred organic solvent is methanol. However, generally, a preferred solvent is a compound with which the formaldehyde forms a weak or strong complex which reduces the activity of formaldehyde towards polymerization.

The water containing source of formaldehyde is available in the form of formalin. Commercially available formalin contains methanol as a stabilizer.

The content of formaldehyde is not specifically limited, but is preferably 5 to 70% by mass with respect to 100% by mass of water containing source of formaldehyde. When commercially available formalin is used as the water containing source of formaldehyde, the content of formaldehyde is generally 37% by mass or more. When the content of formaldehyde is low, for instance, below 5%, and the formaldehyde is used as a raw material in the reaction of producing (meth)acrylic acid alkyl ester, a sufficient yield is not obtained. When the content of formaldehyde is high, for instance, above 50%, a polymerization reaction of formaldehyde may occur and stability tends to deteriorate. Accordingly, a preferred range for the content of formaldehyde is up to less than 20% by weight, more preferably, 5-18% by weight, most preferably, 5-15% by weight in the water containing source of formaldehyde. When a combined water containing source of formaldehyde and water containing source of separation enhancer is used, the overall formaldehyde level in the combined stream is preferably, 2 to 70% by mass with respect to 100% by mass of the water containing combined stream. Again, a preferred range for the content of formaldehyde is up to less than 20% by weight, more preferably, 3-18% by weight, most preferably, 5-15% by weight in the water containing combined stream.

On the other hand, the content of organic solvent in the combined water containing source of formaldehyde and water containing source of separation enhancer other than formaldehyde is preferably 5 to 90% by mass of 100% by mass of combined water containing source of formaldehyde and water containing source of separation enhancer. When the content of the organic solvent other than formaldehyde is lower than 5% by mass, the formaldehyde may not be sufficiently stable. When the content of the organic solvent other than formaldehyde is higher than 90% by mass, the concentration of the raw material for producing (meth) acrylic acid alkyl ester is lowered, and thus a sufficient yield tends not to be obtained.

In the present invention, when water is separated from water containing source of formaldehyde using a zeolite membrane, separation enhancer is or is preferably added to the water containing source of formaldehyde. Thereby, the dehydration performance is increased. The separation enhancer may be in solution with an organic solvent such as methanol. In addition, the separation enhancer may be in solution with water. Preferably, the separation enhancer is in solution with water and methanol. Accordingly, the separation enhancer may be added as a water containing, and optionally, methanol containing, source of separation enhancer. Accordingly, the combined water containing source of formaldehyde and separation enhancer may contain methanol as well as water.

The content of separation enhancer is preferably 10% by mass or more, more preferably 20% by mass or more, with respect to 100% by mass of water containing source of formaldehyde. When the amount of separation enhancer is lower than 10% by mass, it is hard to obtain a sufficient dehydration performance. The upper limit of the amount of separation enhancer added is not specifically limited, but is preferably 90% by mass or less, and more preferably 80% by mass or less.

The preferred separation enhancers are preferably medium polarity solvents.

Suitable separation enhancers may be selected from trifluoromethane, m-difluorobenzene, fluorobenzene, trifluoromethylbenzene, o-fluorotoluene, m-fluorotoluene, p-fluorotoluene, 1,3-bis(trifluoromethyl)benzene; methyl methanoate, ethyl methanoate, methyl ethanoate, methyl acrylate, propyl methanoate, ethyl ethanoate, methyl propanoate, ethyl acrylate, methyl trans-2-butenoate, methyl methacrylate, dimethyl malonate, butyl methanoate, isobutyl methanoate, propyl ethanoate, ethyl propanoate, methyl butanoate, ethyl 2-butenoate ethyl methacrylate, diethyl oxalate, dimethyl succinate, ethylene glycol diacetate, pentyl methanoate, isopentyl methanoate, butyl ethanoate, tert-butyl ethanoate, propyl propanoate, ethyl butanoate, methyl pentanoate, ethylene glycol monoethyl ether acetate, cyclohexyl methanoate, butyl acrylate, diethyl malonate, dimethyl glutarate, 1,2,3,-propanetriol-1,3-diacetate, pentyl ethanoate, butyl propanoate, propyl butanoate, ethyl pentanoate, ethyl 3-methylbutanoate, methyl hexanoate, benzyl methanoate, phenyl ethanoate, methyl benzoate, methyl salicylate, diethyl maleate, diethyl fumarate, methyl cyclohexanecarboxylate, cyclohexyl ethanoate, diisopropyl oxalate, diethyl succinate, dimethyl adipate, hexyl ethanoate, pentyl propanoate, isopentyl propanoate, butyl butanoate, propyl pentanoate, ethyl hexanoate, methyl heptanoate, ethyl benzoate, methyl 4-methylbenzoate, benzyl ethanoate, phenyl propanoate, ethyl salicylate, methyl 2-methoxybenzoate, triacetin, cyclohexyl propanoate, ethyl cyclohexanecarboxylate, diethyl glutarate, heptyl ethanoate, pentyl butanoate, methyl octanoate, methyl 2-(acetyloxy)benzoate, dimethyl phthalate, 2-phenylethyl ethanoate, benzyl propanoate, phenyl propanoate, propyl benzoate, ethyl phenylacetate, cyclohexyl butanoate, diethyl adipate, octyl ethanoate, 2-methylheptyl ethanoate, pentyl pentanoate, ethyl trans-cinnamate, benzyl butanoate, phenyl pentanoate, butyl benzoate, pentyl hexanoate, propyl cinnamate, diethyl phthalate, pentyl benzoate, pentyl salicylate, 1-bornyl ethanoate, dibutyl tartrate, phenyl salicylate, hexyl benzoate, diethyl nonanedioate, benzyl benzoate, benzyl salicylate, pentyl cinnamate, diisobutyl adipate, diethyl sebacate, phenyl 2-(acetyloxy) benzoate, tributyrin, dibutyl phthalate, 2-naphthyl salicylate, dipentyl phthalate, dicyclohexyl adipate, dibutyl sebacate, dihexyl phthalate, 1,2,3-propanetriyl hexanoate, butyl oleate, dioctyl phthalate, dioctyl sebacate; 2-methyl-2-butanol, 2,2-dimethyl-1-propanol, 1-methylcyclopentanol, 3-hexanol, 3-methyl-3-pentanol, 2-ethyl-1-butanol, o-cresol, cyclohexanemethanol, 2-methylcyclohexanol, 2-heptanol, 3-heptanol, 4-heptanol, 3-methyl-2-hexanol, 2,2-dimethyl-1-pentanol, 2,3-xylenol, 2,4-xylenol, 2,5-xylenol, 2,6-xylenol, 3,4-xyleno, 3,5-xylenol, 1-phenylethanol, 2-octanol, 3-octanol, 4-octanol, 2-methyl-1-heptanol, 4-methyl-1-heptanol, 5-methyl-1-heptanol, 3-methyl-2-heptanol, 5-methyl-2-heptanol, 6-methyl-2-heptanol, 3-methyl-4-heptanol, 2-ethyl-1-hexano, 2,2-dimethyl-1-hexano, 2,2-dimethyl-1-hexanol, 1-phenyl-1-propanol, 2-phenyl-2-propanol, 1-phenyl-2-propanol, 1-nonanol, 2-nonanol, 3-nonano, 1-naphthol, 2-naphthol, 1-phenyl-2-methyl-2-propanol, thymol, 1-decanol, 2-decanol, 3-decanol, 2,2-dimethyl-1-octanol, 1-undecanol, 1-dodecanol, 1-tridecano, 1-tetradecanol; dimethyl ether, ethoxyacetylene, tetrahydrofuran, diethyl ether, ethylene glycol dimethyl ether, tetrahydropyran, 2-methyltetrahydrofuran, phenoxyacetylene, butoxyacetylene, diethylene glycol dimethyl ether, anisole, triethoxymethane, ethyl phenyl ether, 1,2-dimethoxybenzene, 1,3-dimethoxybenzene, 1,4-dimethoxybenzene, triethylene glycol dimethyl ether, eucalyptol, tetraethylene glycol dimethyl ether, 1-methoxynaphthalene; 1,4-cyclohexanedione, 2-octanone, 2-nonanone, di-tert-butyl ketone, 2,6-dimethyl-4-heptanone, 2-decanone, 2-undecanone, 7-tridecanone, 9-heptadecanone, 10-nonadecanone; pentanal, 2,2-dimethylpropanal and 1-heptanal; or selected from the above list excluding C1-C5 alkyl alcohols; or selected from the above list excluding alkyl alcohols; or selected from the above list excluding alcohols.

In addition, the separation enhancer extends to mixtures of two or more of the above listed solvents or mixtures of one or more of the above listed solvents with one or more other solvents which mixtures in either case have relative static permittivity falling within the ranges defined above at 20° C. and atmospheric pressure.

The separation enhancer is preferably a carboxylic acid ester represented by the following formula (IV).

$$R^1\text{---}COOR^2 \quad (IV)$$

In formula (IV), $R^1$ is a hydrogen atom or an organic group, and the organic group is preferably an organic group having 1 to 4 carbon atoms. The organic group is a group essentially having a carbon atom, and for example includes an alkyl group, or an alkoxy group.

$R^2$ is an alkyl group, and the alkyl group is preferably an alkyl group having 1 to 4 carbon atoms.

Specific examples of the carboxylic acid ester include methyl propanoate, methyl methacrylate, methyl acrylate, methyl ethanoate, or ethyl ethanoate. Of these, when methyl propanoate or ethyl ethanoate is used as a separation enhancer, a permeation flux tends to be increased. In addition, methyl propanoate can be used as a raw material of a reaction which produces methyl methacrylate by reaction of formaldehyde and methyl propanoate, and therefore methyl propanoate is particularly preferable in the present invention.

The water containing source of formaldehyde is subjected to dehydration using a zeolite membrane.

The zeolite membrane is a membrane having excellent separation, heat resistance, and chemical resistance properties.

Examples of the zeolite membrane include a Linde Type-A (LTA) zeolite membrane, a T-type (ERI-OFF) zeolite membrane, a X-type (FAU) zeolite membrane, a Y-type (FAU) zeolite membrane, a mordenite (MOR) membrane, a ZSM-5 (MFI) zeolite membrane, a BEA zeolite membrane, a chabazite membrane (CHA), and a silicalite membrane. The structures of these zeolites are described in "The Atlas of Zeolite Framework Types", 6$^{th}$ revised edition, by Ch Baerlocher, L B McCusker and D H Olsen, Elsevier, ISBN 978-0-444-53064-6. Of these, a Linde Type-A zeolite membrane, a T-type zeolite membrane, a chabazite membrane (CHA), a X-type zeolite membrane and a Y-type zeolite membrane are preferable. From the viewpoint that water can be selectively separated from the water containing source of formaldehyde, a Linde Type-A zeolite and a chabazite (CHA) membrane having high Al content is preferable.

In addition, the present invention provides advantageously high flux rates.

Generally, as a zeolite type, the higher the Al content, the more the affinity to water is increased, and the more the dehydration performance tends to be improved.

The concentration of water in the water containing source of formaldehyde is typically 25% by mass or less, more typically, 20% by mass or less. When Linde Type-A zeolite membrane is used as zeolite membrane, from the viewpoint of water resistance thereof, a concentration of water in water containing source of formaldehyde is preferably 15% by mass or less, more preferably 10% by mass or less. When a concentration of water in water containing source of formaldehyde is more than 15% by mass, deterioration of separation performance may occur due to the deterioration of the Linde Type-A zeolite membrane. However, if the concentration of water in the water containing source of formaldehyde is reduced, the permeation flux tends to be reduced. Therefore, the concentration of water in the water containing source of formaldehyde irrespective of membrane is preferably 0.5% by mass or more, more preferably 2% by mass or more, and even more preferably 5% by mass or more based on 100% by mass of the water containing source of formaldehyde.

The amount of zeolite is sufficient to dehydrate the water containing source of formaldehyde by preferably at least 10%, more preferably at least 20%, and most preferably at least 30%. Typically, more than 50% of the total water present is separated from the water containing source of formaldehyde.

Generally, the higher the Si/Al molar ratio in a zeolite composition, the more the water separation performance tends to decrease. In comparison with Linde Type-A zeolite (Si/Al≈1.0), T-type zeolite (Si/Al=3.6) and a mordenite (Si/Al=5.1) have a lower water separation performance. The Si:Al molar ratio ranges for the zeolite membrane are preferably between 1:1 and 10:1, more preferably between 1:1 and 9:1.

The Linde Type-A zeolite membrane can be formed by precipitating Linde Type-A zeolite crystals on the surface of a porous support.

Examples of the porous support include ceramics such as alumina, silica, zirconia, silicon nitride, and silicon carbide, metals such as aluminum and stainless steel, and polymers such as polyethylene, polypropylene, and polytetrafluoroethylene. From the viewpoint of the separation performance of the membrane, inorganic compounds such as ceramics or metals are preferable. The shape of the porous support is not specifically limited, but a tube shape is preferable.

A method where a Linde Type-A zeolite crystal is precipitated on the surface of a porous support includes a method in which a Linde Type-A zeolite seed crystal is applied on the surface of the support, followed by precipitation by a synthesis method such as a hydrothermal synthesis method or a vapor phase method, in the presence of a silica raw material (for example, sodium silicate, silica gel, silica sol, silica powder, or the like) and/or an alumina raw material (for example, sodium aluminate, aluminum hydroxide, or the like). The Linde Type-A zeolite can be in the form of its sodium salt in which form it is usually synthesized or can be ion exchanged with solutions of metal ions, for examples, chloride or nitrate salts, particularly potassium or calcium ions or mixtures of these with sodium ions. Preferably part of the sodium ions are ion exchanged with calcium ions to produce the structure known as Linde Type-5A zeolite. Most preferably the Linde Type-A zeolite is in the 100% sodium form known as Linde Type-4A zeolite.

X-type and Y-type zeolites are preferably in their sodium forms or acid forms, more preferably, the sodium forms.

Chabazite type zeolites may be preferably in the form of acid, sodium, potassium, calcium or strontium, more preferably sodium, potassium or calcium. A commercially available product can be used as the Linde Type-A zeolite membrane.

As mentioned above, a method of separating water from a water containing source of formaldehyde using a zeolite membrane includes pervaporation, or vapor permeation. From the viewpoint that the size of the device can be reduced, pervaporation is preferable, whereas from the viewpoint that consumption of heat energy can be lowered without being associated with phase transition, vapor permeation is preferable.

As described above, in dehydration by a zeolite membrane, a separation factor and a permeation flux tend to be increased in accordance with increase of a concentration of water in the water containing source of formaldehyde. Generally, a permeation flux tends to be increased in accordance with the rising of temperature of the water containing source.

In the present invention, the temperature of the water containing source of formaldehyde during separation is preferably 0 to 200° C., more preferably, 30 to 180° C., and most preferably 50 to 150° C.

One example of pervaporation will be specifically described using FIG. 1.

FIG. 1 shows a separator 10 for separating water from the water containing source of formaldehyde using a zeolite membrane by pervaporation. The separator 10 of the example includes a vessel 11 storing an water containing source of formaldehyde, a zeolite membrane 12 provided in the vessel 11, and a thermometer 13, a thermostatic bath 14 for maintaining the constant temperature of the water containing source of formaldehyde in the vessel 11, a vacuum pump 15 for reducing pressure inside the decompression line 16 and the zeolite membrane 12, a decompression line 16 connecting the zeolite membrane 12 to vacuum pump 15, a first collection device 17 and a second collection device 18 provided in the decompression line 16 and a vacuum In the zeolite membrane 12, one end is sealed and the other end is connected to the decompression line 16 through a plug 12a such as a stainless steel tube.

Examples of the thermometer 13 include a thermocouple, or the like.

A first collection device 17 and second collection device 18 collect components (permeation solution) separated from the water containing source of formaldehyde. These devices include Dewar flasks 17a and 18a, which store a refrigerant for cooling components which permeate a zeolite membrane 12 in a vapor state and pass through the first and the second collection devices 17 and 18, and trapping tubes 17b and 18b for trapping the component (permeation solution) in a cooled liquid state or solid state. Examples of the refrigerant include liquid nitrogen.

Specific examples of the pervaporation using a separator 10 shown in FIG. 1 will be described. A case using the Linde Type-A zeolite membranes as a zeolite membrane 12 is described below.

First, the water containing source of formaldehyde is stored in a vessel 11. The temperature of the water containing source of formaldehyde in the vessel 11 is maintained by thermostatic bath 14 so as to be constant. The temperature of the water containing source of formaldehyde is preferably 50 to 150° C. In the specific examples below it is 60° C.

Separately, liquid nitrogen is stored in Dewar flasks 17a and 18a.

Then, a vacuum pump 15 operates to reduce the pressure of an inner portion of a decompression line 16 and the zeolite membrane 12. Then, water in the water containing source of formaldehyde permeates the zeolite membrane 12 in the form of vapor. The water vapor permeating the zeolite membrane 12 is cooled by liquid nitrogen filled in the Dewar flask 17a in a first collection device 17 and collected by a trap tube 17b.

The second collection device 18 need not be provided. However, when the second collection device 18 is provided, in a case where water vapor is not collected by the first collection device 17, the water vapor passing therethrough can be collected by the second collection device 18, and thus infiltration of water into the vacuum pump 15 can be suppressed.

In order to realize efficient membrane separation, it is necessary to provide a concentration difference in the water at the supply side and at the permeation side in respect to the zeolite membrane. As a specific device for providing a concentration difference, one providing a pressure difference which is as large as possible between the permeation and supply sides, or one flowing gas other than water so as not to retain water on the permeation side, can be exemplified.

For providing as large a pressure difference as possible, the supply side may be pressurized, or the permeation side may be depressurized. In consideration of ease and permeability, the pressure of the supply side is preferably 50 to 800 kPa, the pressure of the permeation side is preferably 15.0 kPa or lower, the pressure of the supply side is more preferably atmospheric pressure to 500 kPa, and the pressure of the permeation side is more preferably 5.0 kPa or lower.

As the gas other than water so as not to retain water in the permeation side, in consideration of inertness not reacting with water and ease of availability, nitrogen or argon is preferable.

According to the aforementioned method, water can be separated from the water containing source of formaldehyde. The separated water is collected in a trapping tube 17b of the first collection device 17. On the other hand, the dehydrated source of formaldehyde is stored in a vessel 11.

The aforementioned method permeates water into a zeolite membrane 12, and separates the water from the water containing source of formaldehyde, however, the present invention is not limited thereto. For example, when kinds of the zeolite membrane 12 are changed, components other than water can be made to permeate the zeolite membrane 12 and separate from the water containing source of formaldehyde. In this case, the dehydrated source of formaldehyde is collected in the trapping tube 17b of the first collection device 17 as the permeation solution and water may be retained as the retentate.

The term "a source of formaldehyde" is that free formaldehyde may either form in situ from the source under reaction conditions or that the source may act as the equivalent of free formaldehyde under reaction conditions, for example it may form the same reactive intermediate as formaldehyde so that the equivalent reaction takes place. For the avoidance of doubt the source may itself be free formaldehyde.

A suitable source of formaldehyde may be a compound of formula (V),

wherein $R^5$ and $R^6$ are preferably independently selected from $C_1$-$C_{12}$ hydrocarbons or H, X is O, n is an integer from 1 to 100, and m is 1.

$R^5$ and $R^6$ are independently selected from $C_1$-$C_{12}$ alkyl, alkenyl or aryl as defined herein, or H, more preferably $C_1$-$C_{10}$ alkyl, or H, most preferably $C_1$-$C_6$ alkyl or H, and especially methyl or H. n is an integer preferably from 1 to 10, more preferably 1 to 5, and especially 1 to 3.

However, other sources of formaldehyde may be used including trioxane or trioxane containing sources.

Therefore, a suitable source of formaldehyde includes any equilibrium composition which may provide a source of formaldehyde. Examples of such include but are not restricted to dimethoxymethane, trioxane, polyoxymethylenes $R^1$—O—$(CH_2$—O$)_i$—$R^2$ wherein $R^1$ and/or $R^2$ are alkyl groups or hydrogen, i=1 to 100, paraformaldehyde, formalin (formaldehyde, methanol, water) and other equilibrium compositions such as a mixture of formaldehyde, methanol and methyl propanoate.

Typically, the polyoxymethylenes are higher formals or hemiformals of formaldehyde and methanol $CH_3$—O—$(CH_2$—O$)_i$—$CH_3$ ("formal-i") or $CH_3$—O—$(CH_2$—O$)_i$—H ("hemiformal-i"), wherein i=1 to 100, preferably i=1 to 5, and especially i=1 to 3, or other polyoxymethylenes with at least one non methyl terminal group. Therefore, the source of formaldehyde may also be a polyoxymethylene of formula $R^{31}$—O—(CH2-O—$)_i$ $R^{32}$, where $R^{31}$ and $R^{32}$ may be the same or different groups and at least one is selected from a $C_1$-$C_{10}$ alkyl group, for instance $R^{31}$=isobutyl and $R^{32}$=methyl.

Preferably, the term formalin is a mixture of formaldehyde:methanol:water in the ratio 25 to 65%:0.01 to 25%:25 to 70% by weight. More preferably, the term formalin is a mixture of formaldehyde:methanol:water in the ratio 30 to 60%:0.03 to 20%:35 to 60% by weight. Most preferably, the term formalin is a mixture of formaldehyde:methanol:water in the ratio 35 to 55%:0.05 to 18%:42 to 53% by weight. Preferably, the mixture comprising formaldehyde, methanol and methyl propanoate contains less than 50% water by weight. More preferably, the mixture comprising formaldehyde, methanol and methyl propanoate contains less than 20% water by weight. Most preferably, the mixture comprising formaldehyde, methanol and methyl propanoate contains 0.1 to 15% water by weight.

Typically, the water containing source of formaldehyde is a formaldehyde solution comprising formaldehyde, water and, optionally, methanol. It should be appreciated that the source of formaldehyde may not contain water, for instance where it is in the form of trioxane or free formaldehyde, but water may be added by mixing this stream with a second water containing source of formaldehyde and/or with a water containing source of the separation enhancer, such as wet methyl propanoate.

The dehydrated source of formaldehyde obtained by the process of the present invention, either as permeate or as retentate from which water has been removed as permeate, may be advantageously used as a raw material for producing (meth)acrylic acid alkyl ester.

A method of producing (meth)acrylic acid alkyl ester will be described below as an example.

(Meth)acrylic acid alkyl ester may be obtained by reacting carboxylic acid ester and formaldehyde in the presence of a catalyst in a vapor-phase condensation reaction. Therefore, it is possible to use a dehydrated source of formaldehyde obtained by the present invention as raw material for the reaction. Since water is sufficiently removed from the dehydrated source of formaldehyde, the undesirable introduction of water into the reaction system can be reduced. Therefore, suppression of the progression of the reaction and deterioration of the catalyst does not easily occur.

Examples of the catalyst for this vapor-phase condensation reaction include base catalysts, specifically a catalyst where alkali metals such as potassium, rubidium, and cesium are supported on carriers such as silica, alumina, zirconia, hafnia and combinations thereof.

A suitable molar ratio of carboxylic acid ester to formaldehyde in the vapor-phase condensation reaction is 1:1 to 20:1.

The reaction temperature of the vapor-phase condensation reaction is preferably 250 to 400° C. and the reaction pressure is preferably $1\times10^5$ to $1\times10^6$ Pa.

Advantageously, when the dehydrated source of formaldehyde contains formaldehyde and carboxylic acid ester, and when the molar ratio in the dehydrated source of formaldehyde is within the aforementioned ratio for the vapor-phase condensation reaction, lower levels of or no carboxylic acid ester raw material need be added during the reaction. When the ratio of carboxylic acid ester in the dehydrated solution is too low or absent, carboxylic acid ester is added separately to the dehydrated solution to achieve the necessary level and the solution is subjected to the vapor-phase condensation reaction.

As the carboxylic acid ester added to the dehydrated source of formaldehyde, the carboxylic acid ester mentioned in the dehydration method of water containing source of formaldehyde can be exemplified. The carboxylic acid ester added to the dehydrated source of formaldehyde is preferably the same as the carboxylic acid ester added to the water containing source in the dehydration of the water containing source of formaldehyde.

As the carboxylic acid ester added to the dehydrated source of formaldehyde, a commercially available product or a synthetic compound may be used.

The synthesis method of carboxylic acid ester is not specifically limited, but a synthesis method will be described by an example of methyl propanoate.

Ethylene and methanol are reacted with carbon monoxide in the presence of a catalyst to obtain methyl propanoate (liquid-phase homogeneous reaction).

Examples of the catalysts include a precious metal complex catalyst, specifically a complex catalyst or the like coordinating phosphine or the like to precious metal.

A reaction temperature of liquid-phase homogeneous reaction is preferably 10 to 150° C.

A vapor-phase condensation reaction produces water in addition to (meth)acrylic acid alkyl ester which is objective substance by reacting carboxylic acid ester and formaldehyde. The (meth)acrylic acid alkyl ester is hydrolyzed by water producing the alcohol appropriate to the starting ester. Therefore, vapor-phase condensation reaction is preferably performed in the presence of the appropriate alcohol for suppressing hydrolysis of (meth)acrylic acid alkyl ester.

When as the carboxylic acid ester, methyl propanoate produced by the aforementioned liquid-phase homogeneous reaction is added to the dehydrated source of formaldehyde and subjected to vapor-phase condensation reaction, methanol is used in excess, in comparison with ethylene, and therefore the resultant methyl propanoate contains unreacted methanol. Since the vapor-phase condensation reaction is preferably performed in the presence of alcohol, the unreacted methanol need not be separated from methyl propanoate, and may be provided in the vapor-phase condensation reaction in addition to methyl propanoate.

The dehydrated source of formaldehyde obtained by dehydrating methanol and the water containing source of formaldehyde contains methanol.

Therefore, when the methanol-containing dehydrated solution is used or methyl propanoate produced by a liquid-phase homogeneous reaction is added to the dehydrated solution, the vapor-phase condensation reaction can be performed in the presence of methanol without separate addition of methanol in a reaction system.

The reaction product obtained by vapor-phase condensation reaction contains water in addition to (meth)acrylic acid alkyl ester which is the desired product. In vapor-phase condensation reaction, carboxylic acid ester is used in large excess in comparison with formaldehyde, and therefore the reaction product contains unreacted carboxylic acid ester. Moreover, when vapor-phase condensation reaction is performed in the presence of the alcohol, the reaction product contains the alcohol.

Therefore, (meth)acrylic acid alkyl ester should be separated from the reaction product.

A method for separating (meth)acrylic acid alkyl ester from the reaction product is not specifically limited, and for example the (meth)acrylic acid alkyl ester may be separated by distilling the reaction product.

On the other hand, the residue after separating (meth) acrylic acid alkyl ester from the reaction product contains unreacted carboxylic acid ester and water. Therefore, when carboxylic acid ester and water are separated from the residue, carboxylic acid ester is recovered and recycled as a reactant in the production of (meth)acrylic acid alkyl ester.

The residue of the reaction product above can be used as carboxylic acid ester added to water containing source of formaldehyde in the aforementioned dehydration method of the present invention. Accordingly, dehydration of water containing source of formaldehyde and separation of water from unreacted carboxylic acid ester can be performed at the same time.

The dehydrated source of formaldehyde produced when the residue of reaction product is added to the water containing source of formaldehyde and dehydrated, contains unreacted carboxylic acid ester in addition to formaldehyde. Therefore, when the dehydrated source of formaldehyde is used as raw material of (meth)acrylic acid alkyl ester, unreacted carboxylic acid ester is reused.

The residue of reaction product is added to the water containing source of formaldehyde and dehydrated and the resultant solution containing dehydrated formaldehyde is used as a raw material of (meth)acrylic acid alkyl ester. Thereby, the dehydration method of the present invention can be incorporated into a portion of a method for producing (meth)acrylic acid alkyl ester, whereby production costs can be reduced.

As described above, according to the dehydration method of the present invention, water can be highly efficiently separated from the water containing source of formaldehyde. In particular, when a separation enhancer is added and dehydrated, the dehydration performance is excellent. In this case, if the permeate is enriched in water then the retentate is enriched, with respect to the separation enhancer and water containing source of formaldehyde, in formaldehyde and separation enhancer or if the retentate is enriched in water then the permeate is enriched in formaldehyde and separation enhancer. It is preferred that the permeate is enriched in water.

The dehydrated source of formaldehyde obtained by the dehydration method of the present invention is preferable as a raw material of (meth)acrylic acid alkyl ester. In particular, it is preferable when methyl methacrylate is produced from methyl propanoate. Further, when the dehydrated source of formaldehyde is used as a raw material, the introduction of water into the reaction system can be reduced, and therefore, progress of reaction is not easily suppressed and the catalyst is not easily deteriorated.

EXAMPLES

Hereinafter, specific description will be given in regard to the present invention by giving examples. However, the invention is not limited to these.

Preparative Example 1

The Linde Type-4A zeolite membranes were prepared generally in accordance with the examples of EP1930067. Specifically, seed crystals to assist uniform membrane formation were formed on the support. Linde Type-4A zeolite fine particles (seed crystals, particle size: 100 nm) were placed in water and stirred to yield a suspension with a concentration of 0.5% by weight.

The sealed body was used for this example. Specifically, a tubular porous body made of α-alumina and having opening sections at both ends was prepared. The porous body had a mean pore size of 1.3 μm, an outer diameter of 12 mm, an inner diameter of 9 mm and a length of 10 cm. A sealing member was tightly fitted in one opening section of the porous body, and a sealing member penetrated by an open air conduit was tightly fitted in the other opening section.

The sealed body was immersed in the aforementioned suspension. The entire porous body was immersed in the suspension, and the tip of the open air conduit was not immersed in the suspension. The sealed body was immersed in the suspension for 3 minutes. The sealed body was then drawn out at a rate of about 0.2 cm/s. The porous body obtained by removing the sealing members and from the sealed body was dried for 2 hours in a thermostatic bath at 25° C., and then dried for 16 hours in a thermostatic bath at 70° C. to produce a seed crystal-attached porous body.

Sodium silicate, aluminum hydroxide and distilled water were mixed to yield a reaction solution. 1 part by mole of alumina ($Al_2O_3$), 2 parts by mole of silicon dioxide ($SiO_2$) and 2 parts by mole of sodium oxide ($Na_2O$) were added to 150 parts by mole of water to yield a reaction solution. The seed crystal-attached porous body was immersed in the reaction solution and held at 80° C. for 3 hours to form a zeolite membrane on the surface of the seed crystal-attached porous body.

The obtained zeolite membrane was then cleaned with a brush. Further, it was immersed for 16 hours in warm water at 40° C. A Linde Type-4A zeolite membrane was thus obtained.

Preparative Example 2

The T-type zeolite membranes were prepared generally in accordance with the examples of U.S. Pat. No. 6,387,269.

Amorphous silica is introduced with stirring into an aqueous solution comprising sodium aluminate, sodium hydroxide and potassium hydroxide and allowed to age for 48 hours. The composition of the solution corresponds to the following molar ratios: $SiO_2/Al_2O_3$=112, OH—/$SiO_2$=0.77, Na+/(Na++K+)=0.77, and $H_2O$/(Na++K+)=20.75.

Then a porous tubular support whose surface is provided with seed crystals of the T-type zeolite is immersed in the above reaction mixture. The support consisted of "Mullite", had a length of 10 cm, an external diameter of 1.2 cm, a thickness of 1.5 mm, a pore diameter of 1.3 μm and a porosity of 40%. The average size of seed crystals is 100 μm. The quantity of seed crystals on the porous support is 30 mg/cm². The hydrothermal synthesis is carried out for 24 hours at 100° C., followed by rinsing for 12 hours and drying at 70° C.

Preparative Example 3

CHA-type zeolite membranes were prepared generally by hydrothermal synthesis via a secondary growth method on the outer surface of a porous α-alumina support. For the avoidance of doubt, by "CHA-type zeolite" we mean to refer to a zeolite having a CHA structure as defined by the International Zeolite Association (IZA) and is a zeolite having the same structure as naturally-occurring Chabazite.

First, seed crystals were attached to a porous α-alumina support to assist uniform membrane formation.

The following was prepared as a reaction mixture for hydrothermal synthesis in the seeding process. In a mixture containing 12.8 g of 1 mol/L-NaOH aqueous solution and 75 g of water, 0.8 g of aluminum hydroxide (containing 53.5 wt % of $Al_2O_3$, obtained from Aldrich) was added and dissolved with stirring to make a transparent solution. Thereto, 10.8 g of an aqueous N,N,N-trimethyl-1-adamantanammonium hydroxide (TMADAOH) solution (containing 25 wt % of TMADAOH, obtained from Sachem Inc.) was added as an organic template, and 19.2 g of colloidal silica (Snowtex-40, obtained from Nissan Chemicals Industries, Ltd.) was further added. This mixture was stirred for 3 hours. A CHA-type zeolite seed crystal of about 0.5 μm was synthesized hydrothermally at 160° C. for 2 days. A dip-coating technique was used for seeding. Specifically, an inorganic porous support was dipped vertically into a flask containing an aqueous suspension of the CHA-type zeolite crystals at a concentration of 1% by weight for a predetermined time. It was then dried at 100° C. for about 5 hours producing a seed crystal-attached porous body.

The following was prepared as a reaction mixture for membrane hydrothermal synthesis. In a mixture containing 10.5 g of 1 mol/L-NaOH aqueous solution, 7.0 g of 1 mol/L-KOH aqueous solution and 100.0 g of water, 0.88 g of aluminum hydroxide (containing 53.5 wt % of $Al_2O_3$, obtained from Aldrich) was added and dissolved with stirring to make a transparent solution. Thereto, 2.95 g of an aqueous N,N,N-trimethyl-1-adamantanammonium hydroxide (TMADAOH) solution (containing 25 wt % of TMADAOH, obtained from Sachem Inc.) was added as an organic template, and 10.5 g of colloidal silica (Snowtex-40, obtained from Nissan Chemicals Industries, Ltd.) was further added. This mixture was stirred for 2 hours. The support attached with the seed crystal was dipped in the vertical direction in a Teflon (registered trademark) made inner cylinder containing the reaction mixture above and after tightly closing the autoclave, heated at 160° C. for 48 hours under self-generated pressure. The system was allowed to cool, and the support-zeolite membrane composite was taken out of the reaction mixture, washed and then dried at 120° C. for 5 hours or more. The membrane samples were calcined to remove the template at a rate of 0.1-0.5° C./min. Higher temperatures of 450-500° C. were applied for >20 h.

The molar ratio $SiO_2/Al_2O_3$ of the zeolite membrane was measured by SEM-EDX and found to be 17.

Example 1

Formaldehyde (HCHO), water ($H_2O$), methanol (MeOH), and methyl propanoate (MeP) were mixed so that the mass ratio (HCHO:$H_2O$:MeOH:MeP) was 10:9:11:70, to prepare a sample (feed solution). Water was separated from the feed solution in accordance with the following methods by using a separator 10 shown in FIG. 1.

A Linde Type-4A zeolite membrane (manufactured in a manner of preparative example 1 above, effective membrane area: 2.64×10$^{-3}$ m²) as the zeolite membrane 12, and the thermocouples as a thermometer 13 were provided in the vessel 11. One end of the zeolite membrane 12 was sealed, and the other end was connected with the decompression line 16 through the plug 12a made of stainless-steel, then, the zeolite membrane 12 and the vacuum pump 15 were connected by the decompression line 16. Moreover, the first collection device 17, the second collection device 18, and the vacuum gauge 19 were provided at the middle of the decompression line 16.

500 ml of previously prepared feed solution was stored in the vessel 11. Then, the temperature of the feed solution in the vessel 11 was controlled at the thermostatic bath 14 so that the temperature was 60° C.

The liquid nitrogen was stored in the Dewar flasks 17a and 18a respectively.

Then, the vacuum pump 15 was operated for 30 minutes, and pressure inside the decompression line 16 and the zeolite membrane 12 was reduced so that pressure on the permeation side became 3.0 kPa or less. Vapor that permeated the zeolite membrane 12 was cooled in the first collection device 17 with the liquid nitrogen with which Dewar flask 17a was filled, and the permeation liquid was collected in a trap tube 17b.

The separation performance of the zeolite membrane was evaluated to obtain the permeation flux, the concentrations of water in the collected permeate and the separation factor in accordance with the following methods. The results are shown in Table 1.

(1) Permeation Flux

The mass of the permeate that was collected in the trap tube 17b after separation was measured, and the permeation flux was calculated from the following expression (VI). In the expression (VI), "w" is weight of permeate [kg], "A" is the effective membrane area of the zeolite membrane [m$^2$], and "t" is the permeation time [h]. This permeation flux is an index that shows the weight of permeate per unit area of the membrane, and per unit time.

$$\text{Permeation flux [kg/m}^2\cdot\text{h]}=w/(A\times t) \quad (VI)$$

(2) Concentration of Water in Permeate

The concentration of water in the permeate was obtained by using a gas-chromatograph (detector: TCD (Thermal Conductivity Detector), separation column: porapakQ) at the column temperature of 170° C.

(3) Separation Factor

In the same manner as in the concentration of water in permeate (2) above, the concentration of water in the feed solution was obtained and the separation factor was calculated from the following expression (VII). In the expression (VII), "X" is concentration of water in the feed solution [% by mass], and "Y" is concentration of water in the permeate [% by mass].

$$\text{Separation factor}=\{Y/(100-Y)\}/\{X/(100-X)\} \quad (VII)$$

Example 2

Water was separated again by using the zeolite membrane used in example 1 from the feed solution in the same manner as in example 1. Then, the separation performance in the repetitive use of the zeolite membrane was evaluated. The results are shown in Table 1.

Example 3

Water was separated from the feed solution in the same manner as in example 1, except using an aqueous solution (feed solution) prepared so that the mass ratio in the aqueous solution (HCHO:H$_2$O:MeOH:MeP) became 10:9:41:40. Then, the separation performance of the zeolite membrane was evaluated. The results are shown in Table 1.

Example 4

Water was separated from the feed solution in the same manner as in example 1, except using an aqueous solution (feed solution) prepared so that the mass ratio in the aqueous solution (HCHO:H$_2$O:MeOH:MeP) became 10:9:61:20. Then, the separation performance of the zeolite membrane was evaluated. The results are shown in Table 1.

Example 5

Water was separated from the feed solution in the same manner as in example 1, except using a T-type zeolite membrane (manufactured in a manner of preparative example 2, effective membrane area: 2.64×10$^{-3}$ m$^2$) as the zeolite membrane, and using an aqueous solution (feed solution) prepared so that the mass ratio in the aqueous solution (HCHO:H$_2$O:MeOH:MeP) became 10:9:41:40. Then, the separation performance of the zeolite membrane was evaluated. The results are shown in Table 1.

Example 6

Water was separated from the feed solution in the same manner as in example 1, except methyl ethanoate (MeAc) instead of the MeP, and using an aqueous solution (feed solution) prepared so that the mass ratio in the aqueous solution (HCHO:H$_2$O:MeOH:MeAc) became 10:9:41:40. Then, the separation performance of the zeolite membrane was evaluated. The results are shown in Table 1.

Example 7

Water was separated from the feed solution in the same manner as in example 1, except using methyl methacrylate (MMA) instead of the MeP, and using an aqueous solution (feed solution) prepared so that the mass ratio in the aqueous solution (HCHO:H$_2$O:MeOH:MMA) became 10:9:41:40. Then, the separation performance of the zeolite membrane was evaluated. The results are shown in Table 1.

Example 8

Water was separated from the feed solution in the same manner as in example 1, except using an aqueous solution (feed solution) prepared so that the mass ratio in the aqueous solution (HCHO:H$_2$O:MeOH:MeP) became 11:0.6:12:76.4. Then, the separation performance of the zeolite membrane was evaluated. The results are shown in Table 1.

Example 9

Water was separated from the feed solution in the same manner as in example 1, except using an aqueous solution (feed solution) prepared so that the mass ratio in the aqueous solution (HCHO:H$_2$O:MeOH:MeP) became 11:3:12:74. Then, the separation performance of the zeolite membrane was evaluated. The results are shown in Table 1.

Example 10

Water was separated from the feed solution in the same manner as in example 1, except using an aqueous solution (feed solution) prepared so that the mass ratio in the aqueous solution (HCHO:H$_2$O:MeOH:MeP) became 10:6:11:73. Then, the separation performance of the zeolite membrane was evaluated. The results are shown in Table 1.

Example 11

Water was separated from the feed solution in the same manner as in example 1, except the temperature of the feed solution was adjusted to 50° C. Then, the separation performance of the zeolite membrane was evaluated. The results are shown in Table 1.

Example 12

Water was separated from the feed solution in the same manner as in example 1, except the temperature of the feed solution was adjusted to 40° C. Then, the separation performance of the zeolite membrane was evaluated. The results are shown in Table 1.

Example 13

Water was separated from the feed solution in the same manner as in example 1, except using an aqueous solution (feed solution) prepared by mixing HCHO, $H_2O$ and MeOH so that the mass ratio (HCHO:$H_2O$:MeOH) became 10:9:81. Then, the separation performance of the zeolite membrane was evaluated. The results are shown in Table 1.

Example 14

Water was separated from the feed solution in the same manner as in example 1, except using an aqueous solution (feed solution) prepared by mixing HCHO, $H_2O$, MeOH and MeP so that the mass ratio (HCHO:$H_2O$:MeOH:MeP) became 6:9:15:70. Then, the separation performance of the zeolite membrane was evaluated. The results are shown in Table 1.

Example 15

Water was separated from the feed solution in the same manner as in example 14, except using an aqueous solution (feed solution) prepared by mixing HCHO, $H_2O$, MeOH and 1-pentanol so that the mass ratio (HCHO:$H_2O$:MeOH:1-Pentanol) became 6:9:15:70. Then, the separation performance of the zeolite membrane was evaluated. The results are shown in Table 1.

Example 16

Water was separated from the feed solution in the same manner as in example 14, except using an aqueous solution (feed solution) prepared by mixing HCHO, $H_2O$, MeOH and 1,4-butanediol so that the mass ratio (HCHO:$H_2O$:MeOH:1,4-Butanediol) became 6:9:15:70. Then, the separation performance of the zeolite membrane was evaluated. The results are shown in Table 1.

Example 17

Water was separated from the feed solution in the same manner as in example 14, except using an aqueous solution (feed solution) prepared by mixing HCHO, $H_2O$, MeOH and glycerol (1,2,3-trihydroxypropane) so that the mass ratio (HCHO:$H_2O$:MeOH:Glycerol) became 6:9:15:70. Then, the separation performance of the zeolite membrane was evaluated. The results are shown in Table 1.

TABLE 1

| | Zeolite membrane | Temperature [° C.] | Feed solution | | Permeation flux [kg/m2 × h] | Concentration of water in the permeate [% by mass] | Separation factor |
|---|---|---|---|---|---|---|---|
| | | | Composition | Concentration of water [% by mass] | | | |
| Example 1 | Linde Type-4A | 60 | HCHO/$H_2O$/MeOH/MeP = 10/9/11/70 | 9.0 | 2.61 | 99.98 | 40000 |
| Example 2 | Linde Type-4A | 60 | HCHO/$H_2O$/MeOH/MeP = 10/9/11/70 | 9.0 | 2.46 | 99.97 | 31000 |
| Example 3 | Linde Type-4A | 60 | HCHO/$H_2O$/MeOH/MeP = 10/9/41/40 | 9.0 | 1.75 | 99.93 | 15000 |
| Example 4 | Linde Type-4A | 60 | HCHO/$H_2O$/MeOH/MeP = 10/9/61/20 | 9.0 | 1.45 | 99.8 | 5000 |
| Example 5 | T-Type | 60 | HCHO/$H_2O$/MeOH/MeP = 10/9/41/40 | 9.0 | 0.21 | 98.68 | 760 |
| Example 6 | Linde Type-4A | 60 | HCHO/$H_2O$/MeOH/MeAc = 10/9/41/40 | 9.0 | 1.3 | 99.91 | 12000 |
| Example 7 | Linde Type-4A | 60 | HCHO/$H_2O$/MeOH/MMA = 10/9/41/40 | 9.0 | 1.65 | 99.93 | 14000 |
| Example 8 | Linde Type-4A | 60 | HCHO/$H_2O$/MeOH/MeP = 11/0.6/12/76.4 | 0.6 | 0.33 | 88.57 | 1300 |
| Example 9 | Linde Type-4A | 60 | HCHO/$H_2O$/MeOH/MeP = 11/3/12/74 | 3.0 | 1.35 | 99.37 | 5100 |
| Example 10 | Linde Type-4A | 60 | HCHO/$H_2O$/MeOH/MeP = 10/6/11/73 | 6.0 | 1.94 | 99.67 | 4700 |
| Example 11 | Linde Type-4A | 50 | HCHO/$H_2O$/MeOH/MeP = 10/9/11/70 | 9.0 | 2.24 | 99.93 | 15000 |
| Example 12 | Linde Type-4A | 40 | HCHO/$H_2O$/MeOH/MeP = 10/9/11/70 | 9.0 | 1.77 | 99.88 | 8100 |
| Example 13 | Linde Type-4A | 60 | HCHO/$H_2O$/MeOH = 10/9/81 | 9.0 | 0.92 | 99.45 | 1800 |
| Example 14 | Linde Type-4A | 60 | HCHO/$H_2O$/MeOH/MeP = 6/9/15/70 | 9.0 | 2.44 | 99.98 | 50663 |
| Example 15 | Linde Type-4A | 60 | HCHO/$H_2O$/MeOH/1-pentanol = 6/9/15/70 | 9.0 | 2.1 | 99.95 | 20090 |
| Example 16 | Linde Type-4A | 60 | HCHO/$H_2O$/MeOH/1.4-butanediol = 6/9/15/70 | 9.0 | 1.11 | 99.86 | 7131 |
| Example 17 | Linde Type-4A | 60 | HCHO/$H_2O$/MeOH/glycerol = 6/9/15/70 | 9.0 | 0.93 | 99.89 | 9080 |

As is apparent from Table 1, in examples 1 to 13, water was able to be separated from the feed solution (an aqueous solution of formaldehyde) efficiently, and the dehydration performance was excellent. Particularly, the values for the permeation flux and the separation factor in the examples 1 to 4, 6, 7, 11, 12, 14 and 15 in which dehydration was performed using the Linde Type-4A zeolite membrane with containing the separation enhancer in the aqueous solution, were higher and the separation performance (dehydration performance) was improved compared to the example 13 in which dehydration was performed using the Linde Type-4A zeolite membrane without containing the separation enhancer in the aqueous solution.

Moreover, it is confirmed from the results of examples 1 and 2 that the separation performance is maintained excellently even though the zeolite membrane is used again.

Therefore, it is especially preferable to apply the present invention to the process for the production of (meth)acrylic acid alkyl ester comprising reacting carboxylic acid ester with formaldehyde in the presence of a catalyst, wherein a dehydrated source of formaldehyde is used as a raw material for the above reaction.

Example 18

Figure 2:
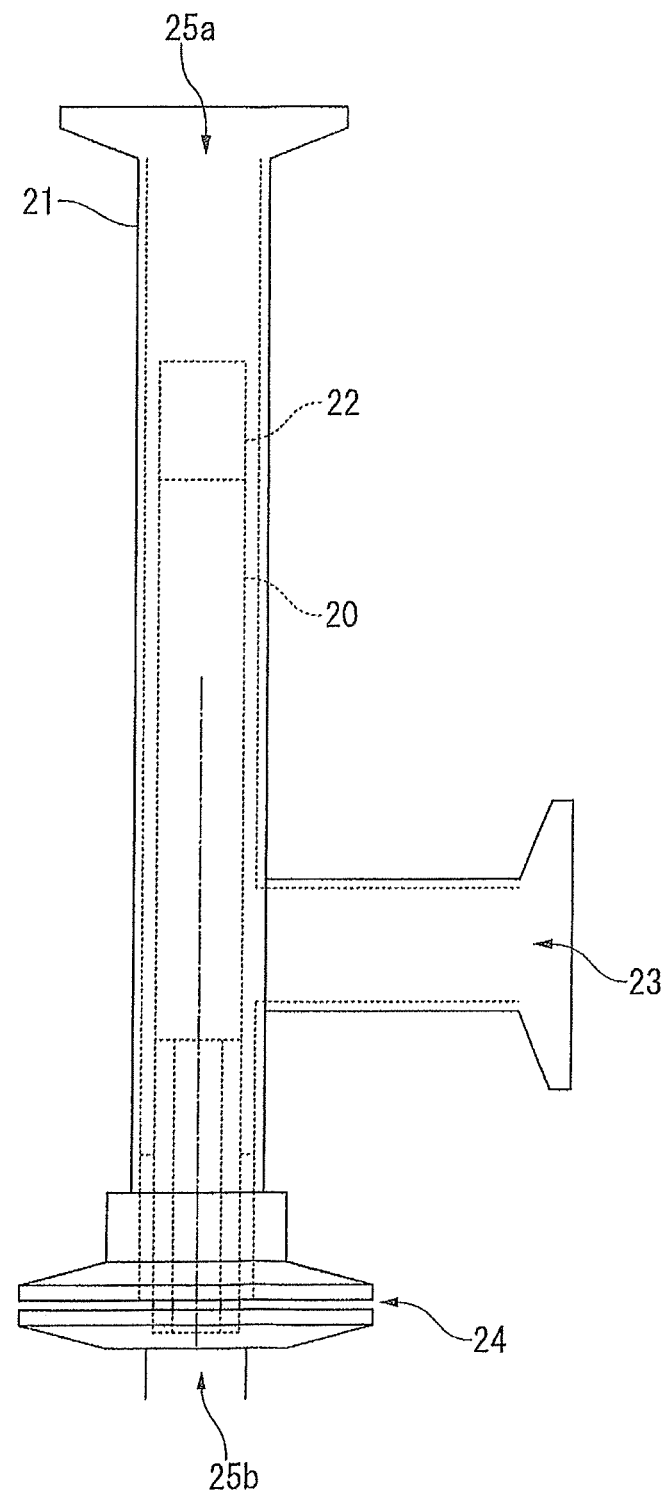
FIG. 2 is a schematic configuration view showing a further example of a separation device where water is separated from the water containing source of formaldehyde.

A feed solution having a HCHO/H$_2$O/MeOH/MeP mass ratio of 5:10:16:66 was fed continuously. Water was separated from the feed solution in accordance with the following method, using a separator as shown in FIG. 2.

A 400 mm CHA-type zeolite membrane 20 (manufactured in a manner of preparative example 3 above,) was housed in a stainless steel housing 21. The top of the membrane which is porous alpha-alumina support was plugged with a solid stainless steel cylinder 22 and sealed. The bottom of the tube, below the side arm 23, was attached to a hollow metal screw-threaded plug 24 and sealed to make a process gas tight seal. The effective area of the exposed 36 mm membrane length was 1.36×10$^{-3}$ m$^2$.

The apparatus was located in an air circulation oven (not shown). Thermally equilibrated feed solution was pumped over the CHA-type zeolite membrane at 1.5 ml/min and 110° C. (3 bar g pressure) through the side arm 23. The feed solution passed upwards over the zeolite membrane surface before exiting through flanged outlet 25a. A vacuum of 3.0. kPa was applied to the outlet 25b at the base of the stainless steel housing 21 to enable components passing through the walls of the membrane 20 (permeate) to be removed out of the apparatus. Permeate liquid was collected into a permeate collection vessel (not shown) and non-permeate liquid was collected in a non-permeate collection vessel (not shown). Liquids in the collection vessels were sampled for analysis. The separation performance of the zeolite membrane was evaluated using analytical methods identical to those described in example 1.

The feed to be dehydrated by the CHA-type zeolite membrane is given in Table 2.

TABLE 2

| Components in Feed | Wt % |
| --- | --- |
| Water | 10.2 |
| Formaldehyde | 4.9 |
| Methanol | 15.7 |
| Formal 1 | 0.23 |
| Isobutyraldehyde | 0.27 |
| Methacrolein | 0.21 |
| Methyl propanoate | 66.23 |
| Methyl isobutyrate | 0.77 |
| Methyl methacrylate | 1.31 |
| Others | 0.18 |

The feed composition was fed continuously for 300 hours and samples of the permeate and non-permeate liquid were collected periodically for analysis. The water content of the non-permeate was measured as 3.0%+/−0.1% throughout the 300 hours. The permeate contained 90% water and 10% methanol with all other components in Table 2 being below their detection limits (typically 10 ppm).

The separation factor, for water with respect to organics between the feed and the permeate as defined in (VII) is 79.2.

The methanol and water in the permeate can easily be separated by a conventional distillation. The level of water in the non-permeate can easily be reduced by increasing the contact time and linear velocity of the solution in contact with the membrane.

INDUSTRIAL AVAILABILITY

The present invention can provide a method for dehydration of the water containing source of formaldehyde having an excellent dehydration performance and a method for producing (meth)acrylic acid alkyl ester by using a dehydrated source of formaldehyde obtained by such dehydration.

REFERENCE SIGNS LIST

10: separator
11: vessel
12: zeolite membrane
12a: plug
13: thermometer
14: thermostatic bath
15: vacuum pump
16: decompression line
17: first collection device
18: second collection device
17a, 18a: Dewar flask
17b, 18b: trap tube
19: vacuum gauge
20: CHA-type zeolite membrane
21: stainless steel housing
22: stainless steel tube over porous α-alumina support
23: side arm
24: screw-threaded plug
25a, 25b: flanged outlets

What is claimed is:
1. A method for producing an ethylenically unsaturated carboxylic ester comprising:
   contacting a dehydrated source of formaldehyde with a carboxylic acid ester in the presence of a catalyst,
   wherein the dehydrated source of formaldehyde is obtained by
   (i) providing a water containing source of formaldehyde, a separation enhancer in an amount of at least 10% by mass or more with respect to 100% by mass of the water containing source of formaldehyde, and methanol, the water containing source of formalde- hyde having a water concentration ranging from 0.5 to 25% by mass of the water containing source of formaldehyde;

(ii) contacting the water containing source of formaldehyde, separation enhancer, and methanol with a zeolite membrane and (iii) separating, by zeolite membrane pervaporation or zeolite membrane vapor permeation, at least 50% of the water from a majority of the water containing source of formaldehyde and from a majority of the separation enhancer to produce the said dehydrated source of formaldehyde, the dehydrated source of formaldehyde including the majority of the separation enhancer therein, wherein the separation enhancer has a static permittivity of between 2.5 and 20 at 20° C. and atmospheric pressure, wherein the separated water of step (iii) is a permeate and the dehydrated source of formaldehyde including the majority of the separation enhancer therein of step (iii) is a retentate; and wherein the temperature of the water containing source of formaldehyde during separation is 0 to 200° C.

2. The method for producing an ethylenically unsaturated carboxylic acid ester according to claim 1, wherein the ethylenically unsaturated acid ester is selected from the group consisting of methyl methacrylate and methyl acrylate.

* * * * *